United States Patent [19]
Parsons, Jr.

[11] Patent Number: 6,028,237
[45] Date of Patent: Feb. 22, 2000

[54] SYNTHESIS OF CYCLOPROPYLACETYLENE

[75] Inventor: Rodney Lawrence Parsons, Jr., Wilmington, Del.

[73] Assignee: DuPont Pharmaceuticals Company, Wilmington, Del.

[21] Appl. No.: 08/990,471

[22] Filed: Dec. 15, 1997

Related U.S. Application Data

[60] Provisional application No. 60/032,981, Dec. 16, 1996.

[51] Int. Cl.[7] .................................. C07C 1/26; C07C 1/28
[52] U.S. Cl. .......................... 585/359; 585/534; 585/641; 585/358; 585/20
[58] Field of Search ................................ 585/359, 534, 585/641, 20, 358

[56] References Cited

U.S. PATENT DOCUMENTS 5,663,467   9/1997   Thompson et al. ..................... 585/359

FOREIGN PATENT DOCUMENTS

WO 9622955   8/1996   WIPO .
WO 9637457   11/1996   WIPO .

OTHER PUBLICATIONS

Thompson et al. (1995) Tetrahedron Letters, vol. 36, No. 49: p. 8937–6940.

*Primary Examiner*—Walter D. Griffin

[57] ABSTRACT

The present invention relates generally to novel methods for the synthesis of cyclopropylacetylene which is a reagent in the asymmetric synthesis of (S)-6-chloro-4-cyclopropylethynyl-4-trifluoromethyl-1,4-dihydro-2H-3,1-benzoxazin-2-one which is a useful human immunodeficiency virus (HIV) reverse transcriptase inhibitor.

19 Claims, No Drawings

SYNTHESIS OF CYCLOPROPYLACETYLENE

This application claims the benefit of U.S. Provisional Application No. 60/032,981, filed Dec. 16, 1996.

FIELD OF THE INVENTION

The present invention relates generally to novel methods for the synthesis of cyclopropylacetylene which is a reagent in the asymmetric synthesis of (S)-6-chloro-4-cyclopropylethynyl-4-trifluoromethyl-1,4-dihydro-2H-3,1-benzoxazin-2-one which is a useful human immunodeficiency virus (HIV) reverse transcriptase inhibitor.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (VI):

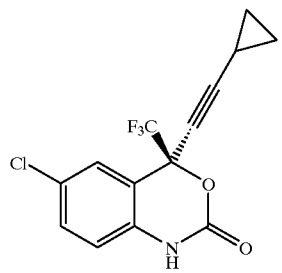

(VI)

is not only a highly potent reverse transcriptase inhibitor, it is also efficacious against HIV reverse transcriptase resistance. Due to the importance of (S)-6-chloro-4-cyclopropylethynyl-4-trifluoromethyl-1,4-dihydro-2H-3,1-benzoxazin-2-one as a reverse transcriptase inhibitor, economical and efficient synthetic processes for its production need to be developed.

Cyclopropylacetylene is an important reagent in the synthesis of compound (VI). Thompson et al, *Tetrahedron Letters* 1995, 36, 937–940, describe the asymmetric synthesis of an enantiomeric benzoxazinone by a highly enantioselective acetylide addition followed by cyclization with a condensing agent to form the benzoxazinone shown below.

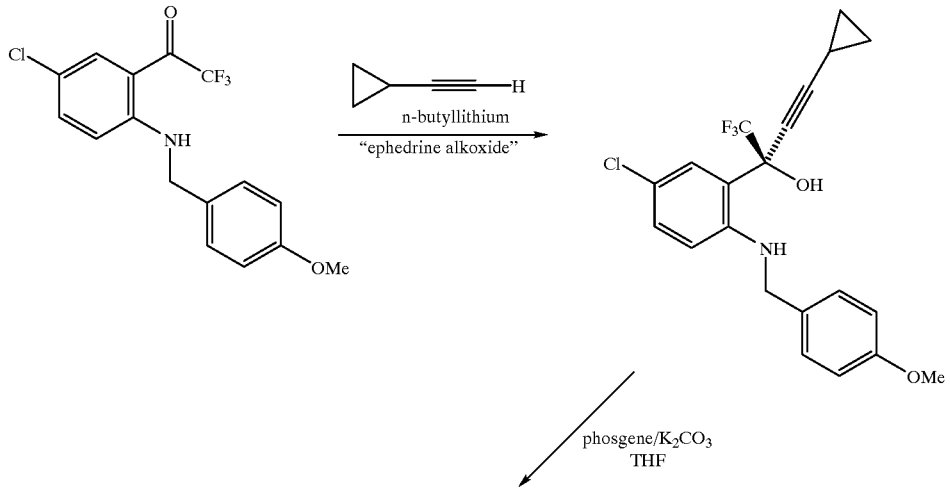

-continued

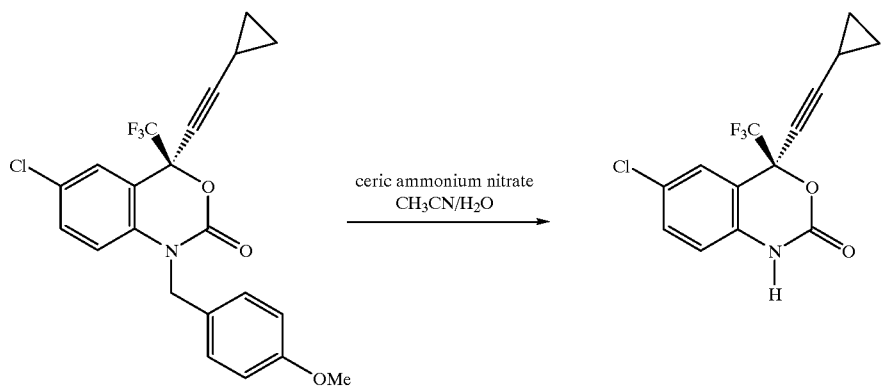

As a reagent the cyclopropylacetylene was synthesized in a 65% yield by cyclization of 5-chloropentyne with n-butyllithium at 0°–80° C. in cyclohexane followed by quenching with ammonium chloride. The process generates a low yield of cyclopropylacetylene which is not feasible for the large commercial process of a difficult to handle reagent.

Thompson et al, PCT International Patent Application Number WO 9622955 A1 describe an improved synthesis of cyclopropylacetylene useful in the synthesis of (S)-6-chloro-4-cyclopropylethynyl-4-trifluoromethyl-1,4-dihydro-2H-3, 1-benzoxazin-2-one. Application Wo 9622955 Al discloses methods which continue to be inefficient in the overall synthesis on a kilogram scale for which this invention makes significant improvements. Application WO 9622955 A1 does not teach the improvement of concentrating cyclopropylacetylene into a high boiling solvent.

The chemical literature shows the majority of the cyclopropylacetylene preparations involve the conversion of cyclopropylmethyl ketone to cyclopropyl-acetylene via the following chemical scheme.

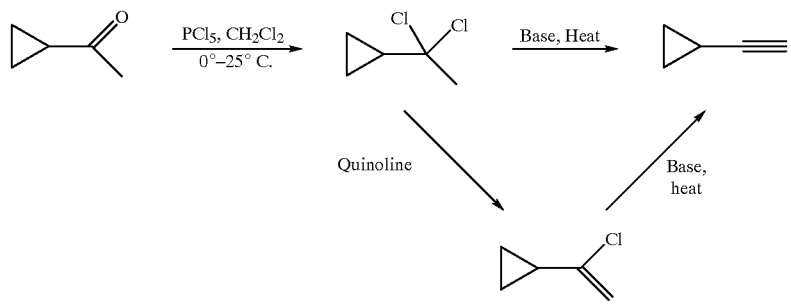

The above method will produce cyclopropylacetylene on small scale, <1 kilogram, but is not amenable for bulk production, thus an alternative was developed.

The above methods for the synthesis of cyclopropylacetylene use combinations of toxic, difficult to handle reagents, relatively expensive materials, incomplete conversions and low yields which render the overall synthesis inefficient and yield cyclopropylacetylene of lower purity. Thus, it is desirable to discover new synthetic routes to cyclopropylacetylene on a large scale which improve upon these limitations and provide high yields of desired cyclopropylacetylene.

Accordingly, the present invention provides for a novel scalable procedure starting with 5-halo-1-pentyne, wherein the conversion of pentyne to cyclopropylethyne is greater than 95%, the overall yield is greater than 90%, the purification of a difficult and tedious volatile product is simplified and the cyclopropylacetylene product is free of acidic materials. The purification and high yield has been simplified by the addition of a concentration step after cyclization of 5-halopentyne into a cyclopropylacetylide anion. This modification allows for the concentration of the volatile cyclopropylacetylene as its non-volatile cyclopropylacetylide salt form. Furthermore, the addition of a concentration step imparts an unexpected safety benefit in the handling of organolithium compounds due to their general explosive and pyrophoretic properties.

Optimization of the procedure allows for streamlined processing since the product does not require isolation. The present invention provides the preparation of cyclopropylacetylene as such pure product that it may be used as a solution stream reagent in the addition of lithium cyclopropylacetylide to any other reagent in synthesis.

None of the above-cited references describe the methods of the present invention for the synthesis of cyclopropylacetylene.

SUMMARY OF THE INVENTION

The present invention concerns improved processes for the preparation of cyclopropylacetylene. In the processes, cyclizing 5-halopentyne into cyclopropylacetylide anion is followed by a concentration step which allows for the easy handling of the volatile cyclopropylacetylene as its non-volatile cyclopropylacetylide salt form before quenching the reaction to produce cyclopropylacetylene. This improvement provides for high conversion of 5-halopentyne into cyclopropylacetylide anion, high overall yields and can be conducted on a kilogram scale.

DETAILED DESCRIPTION OF THE INVENTION

In a first embodiment, the present invention provides a process for the preparation of cyclopropylacetylene comprising:

(1) contacting 5-halo-1-pentyne with a suitable strong base to effect formation of cyclopropylacetylide;

(2) adding a concentration solvent;

(3) distilling the reaction mixture under vacuum to reduce the volume; and (4) contacting the reaction mixture with a suitable quenching agent to effect formation of cyclopropylacetylene.

In a preferred embodiment, the present invention provides a process for the preparation of cyclopropylacetylene comprising:

(1) contacting 5-halo-1-pentyne with a suitable strong base to effect formation of cyclopropylacetylide;

(2) adding a concentration solvent;

(3) distilling the reaction mixture under vacuum to reduce the volume;

(4) contacting the reaction mixture with a suitable quenching agent to effect formation of cyclopropylacetylene;

(5) drying the reaction mixture; and (6) purifying the desired product by distillation.

In a further preferred embodiment, the present invention provides a process for the preparation of cyclopropylacetylene comprising:

(1) contacting 5-halo-1-pentyne with a suitable strong base in a suitable aprotic solvent at a temperature of between about −10° C. and about 30° C. for sufficient time to effect greater than about 95% formation of cyclopropylacetylide;

(2) adding a concentration solvent;

(3) distilling the reaction mixture under vacuum at a temperature of between about 20° C. and about 65° C. to reduce the volume to about one third the volume before distillation under vacuum;

(4) contacting the reaction mixture with a suitable quenching agent to effect formation of cyclopropylacetylene;

(5) drying the reaction mixture; and (6) purifying the desired product by distillation.

In an even further preferred embodiment, the present invention provides a process for the preparation of cyclopropylacetylene comprising:

(1) contacting one equivalent of 5-halo-1-pentyne with about two to about three equivalents of a suitable strong base in a suitable aprotic solvent at a temperature of between about −10° C. and about 30° C. for sufficient time to effect greater than about 95% formation of cyclopropylacetylide;

(2) adding a concentration solvent;

(3) distilling the reaction mixture under vacuum at a temperature of between about 20° C. and about 65° C. to reduce the volume to about one third the volume before distillation under vacuum;

(4) contacting the reaction mixture with a suitable quenching agent to effect formation of cyclopropylacetylene;

(5) drying the reaction mixture to a water content of between about 0 to about 500 parts per million; and (6) purifying the desired product by distillation.

In an even more preferred embodiment, the present invention provides a process for the preparation of cyclopropylacetylene wherein:

the suitable strong base is selected from the group:
 n-hexyllithium, n-butyllithium, s-butyllithium, t-butyllithium, phenyllithium, sodium amide, potassium amide, lithium amide, sodium diethylamide, and sodium dicyclohexylamide;

the suitable aprotic solvent is either an ether solvent or a combination of an ether solvent with one or more hydrocarbon solvents wherein the ether solvent is selected from the group:
 tetrahydrofuran, diethylether, t-butylmethylether, and 1,2-dimethoxyethane; and the hydrocarbon solvent is selected from the group:
 butane, pentane, hexane, heptane, benzene, toluene, and xylene;

the suitable concentration solvent is toluene or methylcyclohexane; and the suitable quenching agent is selected from the group:
 ammonium chloride, ammonium acetate, ammonium sulfate, acetic acid, propionic acid, hydrochloric acid, sulfuric acid and water.

In a second embodiment, the present invention provides a process for the preparation of cyclopropylacetylene comprising:

(1) contacting one equivalent of 5-chloro-1-pentyne with about two to about three equivalents of a n-hexyllithium in either tetrahydrofuran or a combination of tetrahydrofuran/hexane at a temperature of between about −10° C. and about 30° C. for sufficient time to effect greater than about 95% formation of cyclopropylacetylide;

(2) adding toluene;

(3) distilling the reaction mixture under vacuum at a temperature of between about 20° C. and about 65° C. to reduce the volume to about one third the volume before distillation under vacuum;

(4) contacting the reaction mixture with a ammonium chloride to effect formation of cyclopropylacetylene;

(5) drying the reaction mixture to a water content of between about 1 to about 400 parts per million; and (6) purifying the desired product by distillation.

The processes of the present invention are useful for the preparation of (S)-6-chloro-4-cyclopropylethynyl-4-trifluoromethyl-1,4-dihydro-2H-3,1-benzoxazin-2-one, which is useful as a human immunodeficiency virus (HIV) reverse transcriptase inhibitor and compounds which are useful intermediates in the synthesis of (S)-6-chloro-4-cyclopropylethynyl-4-trifluoromethyl-1,4-dihydro-2H-3,1-benzoxazin-2-one. Such HIV reverse transcriptase inhibitors are useful for the inhibition of HIV and the treatment of HIV infection. Such HIV reverse transcriptase inhibitors are useful for the inhibition of HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standards or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The following terms and abbreviations are used herein and defined as follows. The abbreviation:

"THF" as used herein means tetrahydrofuran,
"DMSO" as used herein means dimethylsulfoxide,
"DMAC" as used herein means dimethylacetamide,
"MTBE" as used herein means methyl t-butyl ether,
"BuLi" as used herein means butyllithium,
"NaH" as used herein means sodium hydride, and
"TMEDA" as used herein means tetramethylene ethylendiamine.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable ether solvents include: tetrahydrofuran, diethyl ether, diethoxymethane, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents may include, by way of example and without limitation, ether solvents and hydrocarbon solvents in addition to tetrahydrofuran, 1,4-dioxane, 1,3-dimethyl-3,4,5,6-tetrahydro-2(1H)-pyrimidinone, 1,3-dimethyl-2-imidazolidinone, N-methylpyrrolidinone, hexamethylphosphoramide, triethylamine or ethyl diisopropylamine.

Suitable basic solvents include: 2-, 3-, or 4-picoline, pyrrole, pyrrolidine, morpholine, pyridine, or piperidine.

Suitable hydrocarbon solvents include: butane, pentane, hexane, heptane, octane, nonane, decane, cyclohexane, cycloheptane, methylcyclohexane, indane, ethylbenzene, benzene, toluene, m-xylene, o-xylene, p-xylene or naphthalene.

As used herein, the term "concentration solvent" refers to any solvent which is high boiling, non-acidic and nonreactive. Concentration solvents with boiling points in the range of 65° C. to 200° C. can be used provided the temperature while distilling under vacuum does not exceed 100° C. Efficient concentration solvents preferably have boiling points greater than 80° C. and examples of such include, but are not limited to, cyclohexane, toluene, benzene, heptane, ethylbenzene, cycloheptane, methylcyclohexane, m-xylene, o-xylene, p-xylene, octane, indane, nonane, decane and hexamethylphosphoramide.

As used herein, the term "strong base" refers to any agent which effects the deprotonation of the propargylic carbon (alpha carbon to the alkyne) and cyclization of the resulting anion to effect formation of a three membered cyclopropyl ring. Examples of such strong bases include, but are not limited to, alkyllithiums, metal amides, metal hydrides, metal dialkylamides and arylamines, wherein; alkyllithiums include, isobutyllithium, n-hexyllithium, n-octyllithium, n-butyllithium, s-butyllithium, t-butyllithium, phenyllithium and triphenylmethyllithium; metal amides include sodium amide, potassium amide and lithium amide; metal hydrides include sodium hydride, potassium hydride and lithium hidride; and metal dialkylamides include sodium and potassium salts of methyl, ethyl, n-propyl, i-propyl, n-butyl, t-butyl, trimethylsilyl and cyclohexyl substituted amides.

As used herein, the term "quenching agent" refers to any agent which effects neutralization of a carbon anion by providing a proton and which is inert to reaction with lithium cyclopropylacetylide. Examples of quenching agents include, but are not limited to, ammonium salts, acids and water; wherein examples of such include ammonium chloride, ammonium bromide, ammonium sulfate, ammonium acetate, ammonium phosphate, ammonium tartrate, acetic acid, propionic acid, butanoic acid, tartaric acid, hydrobromic acid, hydrochloric acid, phopshoric acid and sulfuric acid.

As used herein, the term "drying agent" refers to any agent which can effect the removal of water irreversibly from a nonaqueous solvent or combination of nonaqueous solvents, especially after an initial gross predrying by methods such as extraction or phase separation. Examples of drying agents which preferably reduce the concentration of water to less than 500 ppm in the nonaqueous solvent include, but are not limited to, molecular sieves, sodium sulphate, calcium sulphate, magnesium sulphate, calcium chloride and potassium carbonate. Further examples of molecular sieves include 3, 4, 5 and 6A sizes as well as powder, beads or pellets for physical forms.

"Halo" or "halogen" as used herein refers to fluoro, chloro, bromo and iodo. "Alkyl" as used herein is intended to include both branched and straight chain saturated aliphatic hyrdocarbon groups having one to twelve carbon atoms.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

It is the object of the present invention to provide improved processes for the synthesis of cyclopropylacetylene which are useful in the synthesis of benzoxazinones which are useful as HIV reverse transcriptase inhibitors. The methods of the present invention, by way of example and without limitation, may be further understood by reference to Scheme 1. Scheme 1 details the general synthetic method for synthesis of cyclopropylacetylene.

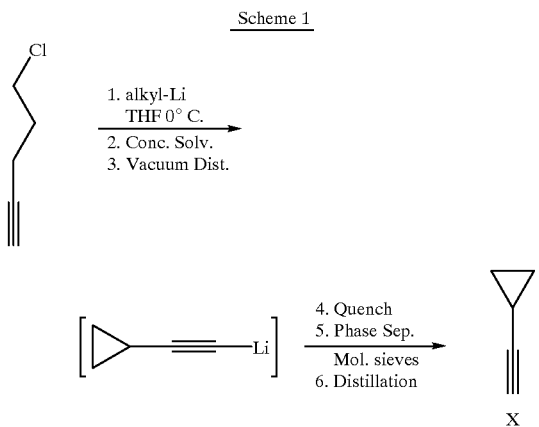

Scheme 1

This reaction as well as close variations, have been run on a 0.7 to 1800 mole scale (in Kilo glassware and pilot plant vessels) in a one pot synthesis.

Prior to Step 1, the vessel is charged with the 5-halo-1-pentyne and an aprotic solvent. The preferred 5-halo-1-pentyne is 5-chloro-1-pentyne. The aprotic solvent is either an ether solvent or a combination of an ether solvent with one or more hydrocarbon solvents wherein the ether solvent is tetrahydrofuran, diethylether, t-butylmethylether or 1,2-dimethoxyethane; and the hydrocarbon solvent is butane, pentane, hexane, heptane, benzene, toluene or xylene. The preferred solvent is tetrahydrofuran. Upon charging the reaction vessel it is then cooled for the strong base addition.

In Step 1 the acetylenic metalation reaction due to the addition of a strong base proceeds instantaneously at about −50° C. to about 100° C., preferably about −10° C. to about 0° C.; while cyclization of the cyclopropyl ring requires aging the solution at about −20° C. to about 100° C., preferably −20° C. to about 30° C., more preferably −20° C. to about 20° C., for a period of about 2 hours. Even more preferably, the reaction temperature starts at about −5° C. and the cyclization occurs at about 0° C. Although a large group of strong bases are possible, alkyl lithiums are preferred of which n-hexyl lithium is most preferred. Note: the temperature of the reaction mixture must remain above −10° C. during the alkyl lithium addition due to an exothermic induction reaction if excess alkyl lithium accumulates at lower temperature. The progress of the cyclization step can be monitored by gas chromatogrqaphic analysis of aliquots quenched with methanol. The reaction was considered complete when the conversion of 5-chloro-1-pentyne to cyclopropylacetylene was greater than 95%, but preferably greater than about 97%.

In Step 1, the stoichiometry of strong base to 5-halo-1-pentyne is about 2:1 to about 10:1. Preferably the number of moles of alkyllithium is about 2 molar equivalents to about 3 molar equivalents due to two acidic sites on 5-halo-1-pentyne. The time for deprotonation and cyclization is about 0.5 hours to about 3 hours.

In Step 2, once the conversion of 5-halo-1-pentyne to cyclopropylacetylene is complete, a concentration solvent is charged. Preferred concentration solvents are heptane, cyclohexane, methylcyclohexane, benzene and toluene; wherein more preferred is toluene or methylcyclohexane due to stability to alkyl lithium reagents above ambient temperatures.

In Step 3, the volume of the solution is reduced by vacuum distillation. Concentration of the reaction mixture at this stage increases the efficiency of the final distillation and removes about 50 to about 75% of the volatile solvent from the reaction mixture. The distillation should be performed expediently due to lower yields with extended heating. It is preferred to reduce the volume to between about ¼ and about ½ of the original solution volume; wherein the more preferred reduction in volume is about ⅓. The temperature during distillation was not allowed rise above about 65° C., is preferably about 0° C. to about 40° C. and more preferably about 25° C. to about 35° C.

It is understood that variations in the choice of concentration solvent and conditions for vacuum distillation in the concentration step are readily determined by one skilled in the art.

In Step 4, the reaction is cooled to about −25 to about 0° C. and the "active lithium" species quenched with a quenching agent. The reaction quench is very exothermic and the resultant heat released can be controlled by the rate of addition of quenching solution never allowing the temperature to rise above 25° C. during addition of the quenching solution. Preferred quenching agents are ammonium chloride, ammonium acetate, ammonium sulfate, acetic acid, propionic acid, hydrochloric acid and sulfuric acid. More preferably the quenching agent is an ammonium salt; even more preferably the ammonium salt is ammonium chloride.

In Step 5, the organic layer containing product cyclopropylacetylene is dried by standard extraction and phase separation techniques followed by drying with a drying agent until the water content of the organic layer is about 0 to about 500 ppm, preferably less than about 400 ppm, by Karl Fisher analysis. Preferred drying agents include molecular sieves, sodium sulfate, magnesium sulfate and calcium chloride. More preferably the drying agent is a molecular sieve; even more preferably the drying agent is a 3Å molecular sieve.

In Step 6, the product is distilled at atmospheric pressure through a column. The column can be packed or unpacked; if packed, the packing material can be any standard material known to one skilled in the art organic synthesis and purification. Preferably the reaction is slowly heated to about the boiling point of the concentration solvent. Preferably the concentration solvent is toluene and the reaction is slowly heated to about 110° C. The final distillate, collected between a head temperature of about 45 to about 110° C., is a volatile, high purity solution of cyclopropylacetylene/ THF/hexane/toluene.

The overall yield was about 90 to about 95% and the product solution strength was about 45 to about 15 wt %.

The present invention, by way of example and without limitation, may be further exemplified in the preparation of compound (X) by reference to Scheme 2.

Scheme 2

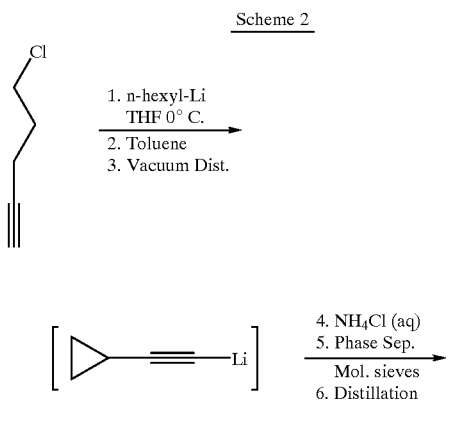

The present invention, by way of example and without limitation, may be further exemplified in the preparation of compound (VI) by reference to Scheme 3.

Scheme 3

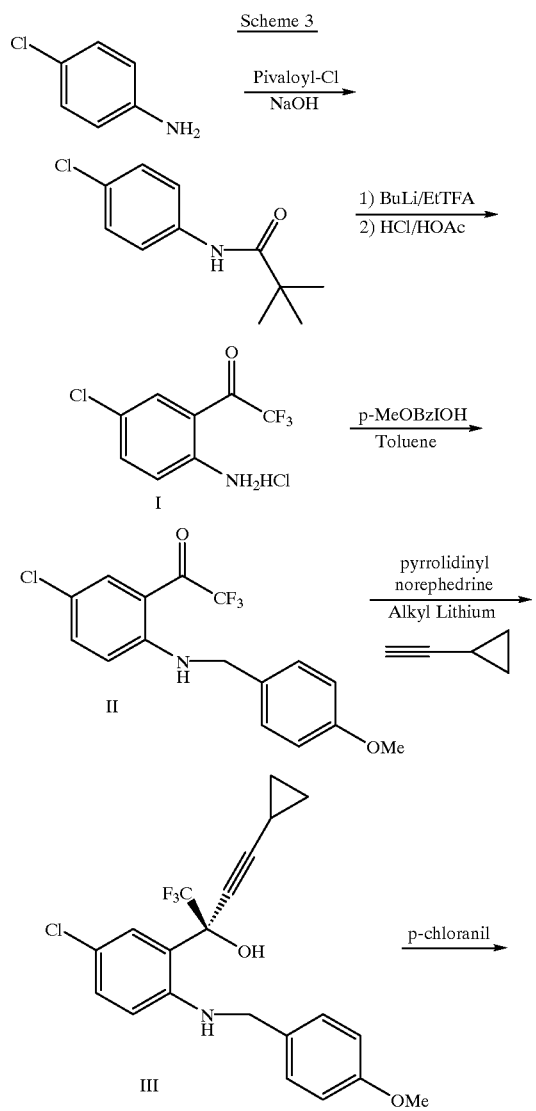

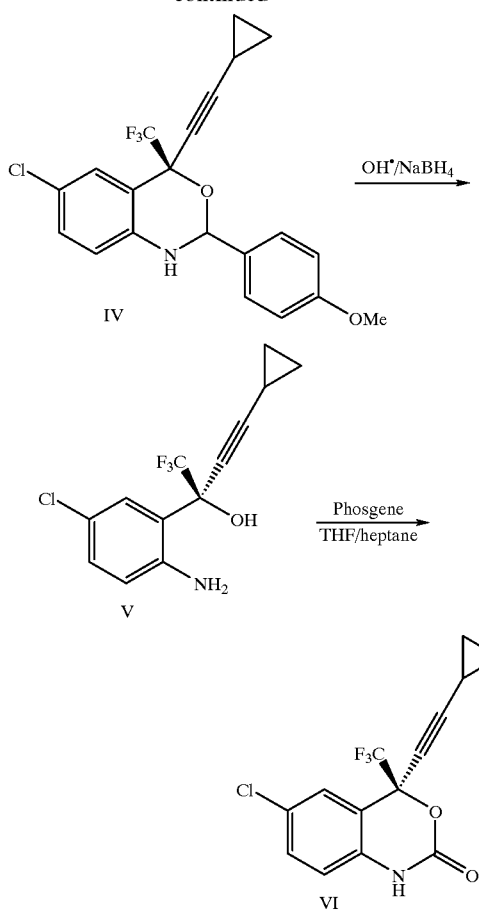

The following examples are meant to be illustrative of the present invention. These examples are presented to exemplify the invention and are not to be construed as limiting the invention's scope.

EXAMPLE 1a

Preparation of Cyclopropylacetylene.

A mixture of 5-chloro-1-pentyne (23.0 kg, 224 mol) and anhydrous THF (150 kg) is cooled to −20° C. n-Hexyllithium (2.3 eq.; 158 kg of 30 wt.%) in hexane is added into the mixture at such a rate as to not allow the temperature to go over 5° C. (approximately 2 hours). During the second half of the n-hexyllithium addition the temperature must remain above −5° C. to prevent an accumulation of the organolithium and a dangerously exothermic induction reaction. The reaction is aged at −5 to 0° C. for 2 hours, until GC analysis indicates at least 99% conversion. Toluene (35 to 40 kg) is then added and the reaction is concentrated under vacuum until the volume is reduced to ~⅓ of original volume. The mixture is heated (to ~40° C.) over the course of the concentration to maintain a good rate of distillation. The mixture is then cooled to 15 to −20° C. and a solution of ammonium chloride (11 to 12 kg) in 50 to 60 L water is added at such a rate as to not allow the temperature to go above 10° C. After separation of the aqueous layer (approximately 70 kg), the reaction mixture is circulated through a tower containing 15 kg of 3Å molecular sieves until the water content is ~300 ppm or lower as determined by Karl Fisher analysis. The dried organic solution is then distilled through a column packed with steel wool at atmospheric pressure, collecting cyclopropylacetylene as a solution in THF/toluene/hexane. The calculated yield is 14.0 kg.

EXAMPLE 1b

Preparation of Cyclopropylacetylene.

A clean, dry 200 gallon reaction vessel was cleaned, dried and inerted. The vessel was charged with THF (200 kg), 5-chloro-1-pentyne (32 kg, 312 mol) and then cooled to −20° C. with high agitation (~175 rpm). Over a period of about four hours, a solution of 33 wt.% n-hexyllithium in hexane (218 kg, 2.5 eq.) was charged into the vessel at such a rate as to keep the mixture temperature between −5° C. and 5° C. The reaction mixture temperature must remain above −10 ° C. during the hexyl lithium addition due to an exothermic induction reaction if excess hexyl lithium accumulates at lower temperature.

The reaction mixture was aged at 0° C. (~2 h) until greater than 97% conversion (by GC analysis) is achieved. The analysis samples are pyrophoric and must be removed under anhydrous and anaerobic conditions and immediately quenched into excess ammonium chloride solution prior to assay. When the assayed conversion was above 97%, toluene (53 kg) was added to the vessel.

The vessel was evacuated (final pressure ~40 torr) with gradual warming (the heating rate brought the reactor to a temperature of 25° C. over one hour) to effect a vacuum distillation of the solvents (concentration time ~6 h). The vacuum distillation should be performed expediently; in order to minimize product decomposition and increase product yield the reaction mixture temperature should remain below 65° C. In addition, the agitation rate should be maintained at ~150 rpm to prevent caking of the reaction salts during the concentration. When the reaction mixture volume had reduced to ⅓ of the original volume the vessel was cooled to −20° C.

An aqueous solution of ammonium chloride (20 kg in 110 L of $H_2O$) was added at such a rate that the temperature did not rise above 5° C. (quench addition time ~3 h). The residual salts were washed from the vessel sides by opening the "man-way" and rinsing the sides with ~15 L of water. The quenched reaction mixture was stirred at 10° C. for 15 minutes.

Agitation was stopped and the phases allowed to separate for 30 minutes. The aqueous layer was separated and the rag layer transferred back to the reaction mixture.

The resulting cooled (−10° C.) organic phase was cycled through a closed cylinder containing ~4.5 kg of 3 Å molecular sieves to remove the remaining water (cycling time ~2 h). Cycling was continued until a water content of <400 ppm (as assayed by Karl Fisher test) was reached. The resultant dry organic solution was then distilled through a packed column (packed with steel turnings, ~4 meters in length) into a cooled receiving flask (−20° C.).

Distill the product by slowly heating the pot to 110° C. Fractions from 45° C. to 110° C. were collected and contain an overall yield of about 90–95% product.

Samples from each fraction and the pot residue were taken for G.C. analysis prior to combination or disposal. The CPA/toluene/hexane/THF mixture is a volatile solution and needs to be stored in a gas tight container in a refrigerator.

EXAMPLE 2

Preparation of N-(4-chlorophenyl)-2,2-dimethyl propanamide. 4-Chloroaniline (52.7 kg, 413 mol) was dissolved in a mixture of t-butyl methyl ether (180 kg), 30% aqueous sodium hydroxide (61.6 kg, 463 mol) and water (24.2 kg), then cooled to 15° C. To the resulting slurry was charged trimethylacetyl chloride (52.2 kg, 448 mol) over 1 h, keeping the temperature below 40° C. After stirring 30 min at 30° C. the slurry was cooled to −10° C. and held for 2 hours. The product was collected by filtration, washed with a solution of 90/10 water/methanol (175 kg), then dried in vacuo to give 85 kg (97% yield) of the title compound as a crystalline solid: mp 152–153° C.; $^1$H NMR (300 MHz, $CDCl_3$) δ7.48 (d, J=9 Hz, 2H) 7.28 (d, J=9 Hz, 2H); $^{13}$C NMR (75 MHz, $CDCl_3$) d 176.7, 136.6, 129.1, 128.9, 121.4, 39.6, 27.6.

EXAMPLE 3

Preparation of 4-Chloro-2-trifluoroacetylaniline, hydrochloride hydrate. N-(4-Chlorophenyl)-2,2-dimethyl propanamide (36.7 kg, 173 mol) was charged to a solution of TMEDA (20.2 kg, 174 mol) in anhydrous t-butyl methyl ether (271.5 kg) and cooled to −20° C. To the cold slurry was added 2.7 N n-butyllithium in hexane (101.9 kg, 393 mol) while keeping the temperature below 5° C. After aging 2 hr at 0 to 5° C., the solution was cooled below −15° C. then rapidly reacted with ethyl trifluoroacetate (34.5 kg, 243 mol). After 30 min, the resulting solution was quenched into 3N HCl (196 L, 589 mol) keeping the temperature below 25° C. After removal of the aqueous phase, the organic solution was concentrated by distilling approximately 200 L of solvent. Acetic acid (352 kg) was added while distilling 325 kg solvent under 100 mm vacuum. After cooling the solution to 30° C., 12 N HCl (43.4 kg, 434 mol) was added and the mixture heated to 65 to 70° C. and held 4 hours. The resulting slurry was cooled to 5° C. and the product was collected by filtration, washed with ethyl acetate (50.5 kg) and dried in vacuo to give 42.1 kg (87%) of the title compound as a white crystalline solid: mp 159–162 dec; $^1$H NMR (300 MHz, DMSO-d6) d 7.65–7.5 (complex, 2H), 7.1 (d, J=8 Hz, 1H), 7.0 (brs, 3H); $^{19}$F NMR (282 MHz, DMSO-$d_6$) δ−69.5.

EXAMPLE 4-a

Preparation of 4-Chloro-2-trifluoroacetyl-aniline. 4-Chloro-2-trifluoroacetylaniline, hydrochloride hydrate (17.1 g, 62 mmol) was stirred in a mixture of toluene (100 mL) and water (50 mL). The mixture was neutralized to pH 7 with saturated $NaHCO_3$. The organic phase was concentrated in vacuo and the residue recrystallized from heptane to give 12.5 g (91%) of the title compound as yellow needles: mp 98–99° C.; $^1$H NMR (300 MHz, $CDCl_3$) δ7.70 (t, J=2 Hz, 1H), 7.32 (dd, J=2, 9 Hz, 1H), 6.7 ( d, J=9 Hz, 1H), 6.44 (brs, 2H); $^{13}$C NMR (75 MHz $CDCl_3$) δ 180.0, 151.6, 136.9, 130.1, 120.9, 119.0, 116.8, 111.4; $^{19}$F NMR (282 MHz, $CDCl_3$) δ-70.3.

EXAMPLE 4

Preparation of N-((4'-Methoxy)benzyl)-4-chloro-2-trifluoroacetylaniline. Compound (II):

To a slurry of 4-Chloro-2-trifluoroacetylaniline, hydrochloride hydrate (40.0 kg, 144 mol) in toluene (140 kg) and water (50L) was added 30% NaOH (18 kg) to pH 7.0. After removing the aqueous phase, 4-methoxybenzyl alcohol (20 kg, 144 mol) and TsOH (1.0 kg, 5.3 mol) were added. The solution was heated to reflux and the water/toluene azeotrope (30L) distilled. The solution was cooled to room temperature and washed with saturated brine (80 kg). The organic solution was concentrated in vacuo to a volume of 35–40L, then diluted with THF (52 kg). The weight percent of the title compound in toluene/THF was calculated by HPLC to be 43%. The yield based on HPLC weight % analysis was 47.7 kg (96%). An analytical sample was obtained by removing the solvent in vacuo and recrystallizing from heptane: mp 82–84° C.; $^1$H NMR (300 MHz, CDCl$_3$) δ9.04 (s,1H), 7.74 (d, J=2 Hz, 1H), 7.35 (dd, J=2, 9 Hz), 7.24 (d, J=8 Hz, 2H), 6.91 (d, J=8 Hz, 2H), 6.75 (d, J=9 Hz, 1H), 4.43 (d, J=6 Hz, 2H), 3.79 (s, 3H); $^{13}$C NMR (75 MHz, CDCl$_3$) δ180.5, 159.2, 151.9, 137.4, 130.8, 128.9, 128.4, 119.9, 117.0, 114.5, 114.4, 111.3, 55.3, 46.6.

EXAMPLE 5

Preparation of (S)-5-Chloro-α-(cyclopropylethynyl)-2-[(4-methoxyphenyl) methyl]-amino]α-(trifluoromethyl) benzenemethanol. Compound (III):

To a toluene solution of (1R,2S)-pyrrolidinyl norephedrine (80 kg, containing 60.7 mol (1R,2S)-pyrrolidinyl norephedrine) was charged triphenylmethane (100 g). The solution was concentrated in vacuo to about half the original volume. Anhydrous THF (35 kg) was added and the solution chilled with the cooling jacket set at −50° C. When the temperature reached −20° C., n-hexyllithium (33 wt % in hexanes, 33.4 kg, 119.5 mol) was charged while maintaining the temperature below 0° C. To the resulting red solution was charged a solution of cyclopropylacetylene (30 wt % in THF/hexanes/toluene; containing about 4 kg, 65 mol of cyclopropylacetylene) while maintaining an internal temperature below −20° C. The resultant solution was aged at −45 to −50° C. for 1 hour. To the cold solution was charged a solution of N-((4'-Methoxy)benzyl)-4-chloro-2-trifluoroacetylaniline (43 wt % in THF/toluene; containing about 10 kg, 28.8 mol of N-((41-Methoxy)benzyl)-4-chloro-2-trifluoroacetylaniline) while maintaining a reaction temperature below −40° C. After aging the mixture at −43 +/−3° C. for 1 h, the reaction was quenched into 140 kg 1N HCl, pre-chilled to 0° C. The organic layer was separated and extracted twice with 25 kg portions of 1N HCl, twice with 40 kg water, then concentrated in vacuo to a volume of about 29L. Toluene (47 kg) was added and the solution concentrated to a volume of 28 to 30L. Heptane (23 kg) was charged and the mixture cooled and held at −5° C. for 4 hours. The product was filtered, washed twice with 10 kg portions of heptane and dried in vacuo to give 10 kg (85%) of the title compound as an off-white solid: mp 163–165° C.; [a]$^{25}$D +8.15° (c 1.006, MeOH); $^1$H NMR (300 MHz, CDCl$_3$) δ 7.55 (brs, 1H), 7.23 (d, J=8 Hz, 2H), 7.13 (dd, J=3, 9 Hz, 1H), 6.86 (d, J=8 Hz, 2H), 6.59 (d, J=8 Hz, 1H), 4.95 (bs, 1H), 4.23 (s, 2H), 3.79 (s, 3H), 2.39 (m, 1H), 1.34 (m, 1H), 0.84 (m, 2H), 0.76 (m, 2H); $^{13}$C NMR (75 MHz, CDCl$_3$) δ158.9, 145.5, 130.6, 130.3, 130.2, 128.6, 125.9, 122.0, 121.6, 119.5, 114.8, 114.1, 94.0, 75.2, 74.7, 70.6, 55.3, 48.0, 8.6, 8.5, −0.6; $^{19}$F NMR (282 MHz, CDCl$_3$) δ −80.19.

EXAMPLE 6

Preparation of (S)-6-Chloro-4-(cyclopropyl-ethynyl)-1,4-dihydro-4-(trifluoromethyl)-2-(4'-methoxyphenyl)-3,1-benzoxazine. Compound (IV):

To a solution of heptane (295.5 kg) and ethyl acetate (32.5 kg) was added p-chloranil (57 kg, 232 mol) and (S)-5-Chloro-α-(cyclopropylethynyl)-2-[(4-methoxyphenyl) methyl]-amino]-α-(trifluoromethyl) benzenemethanol (89 kg, 217 mol). The mixture was refluxed with good agitation for 5.5 h then diluted with ethyl acetate (64.1 kg) and cooled to 30° C. Tetracholorophydroquinone was removed by filtration and washed with a mixture of heptane (104.7 kg) and ethyl acetate (31 kg). The filtrate was partially concentrated by distillation of 260 L solvent, then diluted with heptane (177 kg) and cooled to −10 to −15° C. The resulting slurry was filtered and the product washed with heptane (41 kg) and dried on the filter to less than 20 wt % heptane (by loss on drying). The yield of (IV), calculated by HPLC, was 71 kg (80%). An analytical sample was obtained by trituration of the sample with 1N NaOH, followed by recrystallization from hexane/ethyl acetate: mp 130–131.7° C.; 1H NMR (300 MHz, DMSO-d$_6$) δ7.46 (d, J=9 Hz, 2H),7.28-7.21 (m, 3H), 7.0 ( d, J=9 Hz, 2H), 6.85 (d,J=9 Hz, 1H), 5.52 (s, 1H), 3.78 (s, 3H), 1.52-1.47 (m, 1H), 0.90-0.84 (m, 2H), 0.72-0.68 (m, 1H); $^{13}$C NMR (75 MHz, DMSO-d$_6$) δ160.3, 143.8, 129.6, 129.3, 128.9, 125.8, 123.1, 121.7, 118.1, 117.8, 113.8, 93.6, 80.9, 74.1, 70.3, 55.2, 8.5, 8.4, -1.07; $^{19}$F NMR (282 MHz, CDCl$_3$) δ-157.5.

EXAMPLE 7

Preparation of Compound (V): (S)-5-Chloro-α-(cyclopropylethynyl)-2-amino-α-(trifluoromethyl) benzenemethanol.

Crude (S)-6-Chloro-4-(cyclopropylethynyl)-1,4-dihydro-4-(trifluoromethyl)-2-(4'-methoxyphenyl) -3, 1-benzoxazine (71 kg calculated dry weight) was charged to a mixture of methanol (301 kg), 30% NaOH (121 kg) and water (61L). The mixture was heated to 60° C. to give a clear solution then cooled to 30° C. A solution of sodium borohydride (3.2 kg, 84.2 mol) in 0.2 N NaOH (29L) was added to the methanolic solution over 20 min, keeping the temperature below 35° C. After 30 min, excess borohydride was quenched with acetone (5.8 kg) and the solution diluted with water (175L) then neutralized to pH 8 to 9 with acetic acid. The resulting slurry was cooled to about 0° C., filtered and the product washed with water then dried in vacuo at 40° C. The crude product was reslurried with a mixture of toluene (133 kg) and heptanes (106 kg) initially at 25° C., then with cooling below −10° C. The product was filtered, washed with heptanes (41 kg) and dried in vacuo at 40° C. to give 44.5 kg (88%) as an off-white/pale yellow crystalline solid. An analytical sample was recrystallized from t-butyl methyl ether/heptane: mp 141–143° C.; [a]$^{25}$D −28.3° (c 0.106, MeOH); 1H NMR (300 MHz, CDCl$_3$) δ7.54 (d, J=2 Hz, 1H), 7.13 (dd, J=9, 2 Hz, 1H), 6.61 (d, J=9 Hz, 1H), 4.61 (brs, 1H), 4.40 (brs, 1H), 1.44–135 (m, 1H), 0.94–0.78 (m, 2H): $^{13}$C NMR (75 MHz, DMSO-d$_6$) δ146.7, 129.4, 129.0, 124.3, 118.4, 118.07, 118.05, 92.3, 72.6, 71.0, 8.2, 8.1, -1.1; $^{19}$F NMR (282 MHz CDCl$_3$) δ−80.5.

EXAMPLE 8

Preparation of (S)-6-Chloro-4-(cyclopropyl-ethynyl)-1,4-dihydro-4-(trifluoromethyl)-2H-3,1-benzoxazine-2-one. Compound (VI).

(S)-5-Chloro-α-(cyclopropylethynyl)-2-amino-α-(trifluoromethyl)benzenemethanol (15.7 kg, 54.3 mol) was dissolved in a mixture of heptanes (32 kg) and THF (52 kg) below −10° C. Phosgene (~8.0 kg, 80 mol) was directly fed below the surface over about 1 h, keeping the temperature below 0° C. The resulting slurry was warmed to 20–25° C. and held 1 hour. Methanol (6.5 kg, 203 mol) was added and the solution stirred about 30 min. Heptanes (97 kg) was added and ~140L of solvent was distilled under reduced pressure. Heptanes (97 kg) and THF (22 kg) were added and the solution washed with 5% aqueous sodium bicarbonate (15L), followed by water (15L). The solution was warmed to 50° C. and filtered into a clean reactor, followed by a 40 kg heptanes rinse. The solution was concentrated under reduced pressure, diluted with heptanes (22 kg) and cooled below −10° C. The product was filtered, washed with heptanes (37 kg) and dried in vacuo at 90–100° C. to give 16.0 kg (95%) as an off-white to slightly pinkish solid. HPLC: 99.8 area %: mp 139–141° C.; [a]$^{25}$D −94.1° (c 0.300, MeOH); 1H NMR (400 MHz, DMSO-d$_6$) δ 11.05 (s, 1H), 7.54 (dd, J=2.5, 7 Hz, 1H), 7.43 (d, J=2.5 Hz, 1H), 6.99 (d, J=7 Hz, 1H), 1.58 (m, 1H), 0.92 (m, 2H), 0.77 (m, 2H); $^{13}$C NMR (100 MHz, DMSO-d$_6$) δ146.23, 134.71, 132.04, 126.93, 126.57, 122.24, 116.83, 114.08, 95.63, 77.62, 65.85, 8.48, 8.44, −1.32; $^{19}$F NMR (282 MHz, DMSO-d$_6$) δ-81.1.

Although the present invention has been described with respect to specific embodiments, the details of these embodiments are not to be construed as limitations. Various equivalents, changes and modification may be made without departing from the spirit and the scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

What is claimed is:

1. A process for synthesis of cyclopropylacetylene, said process comprising:
    (1) contacting 5-halo-1-pentyne with a suitable strong base to form a reaction mixture and effect formation of cyclopropylacetylide;
    (2) adding a concentration solvent;
    (3) distilling the reaction mixture under vacuum to reduce the volume; and
    (4) contacting the reaction mixture with a suitable quenching agent to effect formation of cyclopropylacetylene.

2. A process according to claim 1 for synthesis of cyclopropylacetylene, further comprising:
    (1) drying the reaction mixture; and
    (2) purifying the desired product by distillation.

3. A process according to claim 2 for the synthesis of cyclopropylacetylene, wherein:
    the suitable strong base is selected from the group consisting of:
        n-hexyllithium, n-butyllithium, s-butyllithium, t-butyllithium, phenyllithium, sodium amide, potassium amide, lithium amide, sodium diethylamide and sodium dicyclohexylamide;
    the suitable concentration solvent is toluene or methylcyclohexane; and
    the suitable quenching agent is selected from the group consisting of:
    ammonium chloride, ammonium acetate, ammonium sulfate, acetic acid, propionic acid, hydrochloric acid, sulfuric acid and water.

4. A process according to claim 3 for the synthesis of cyclopropylacetylene, wherein:
    the 5-halo-1-pentyne is 5-chloro-1-pentyne;
    the suitable strong base is n-hexyllithium;
    the suitable concentration solvent is toluene; and
    the suitable quenching agent is ammonium chloride.

5. A process according to claim 2 for synthesis of cyclopropylacetylene, comprising:
    (1) contacting 5-halo-1-pentyne with a suitable strong base in a suitable aprotic solvent at a temperature of between about −10° C. and about 30° C. for sufficient time to effect greater than about 95% formation of cyclopropylacetylide;
    (2) adding a concentration solvent;
    (3) distilling the reaction mixture under vacuum at a temperature of between about 20° C. and about 65° C. to reduce the volume to about one third the volume before distillation under vacuum;
    (4) contacting the reaction mixture with a suitable quenching agent to effect formation of cyclopropylacetylene;
    (5) drying the reaction mixture; and
    (6) purifying the desired product by distillation.

6. A process according to claim 5 for the synthesis of cyclopropylacetylene, wherein:
    the suitable strong base is selected from the group consisting of:
        n-hexyllithium, n-butyllithium, s-butyllithium, t-butyllithium, phenyllithium, sodium amide, potassium amide, lithium amide, sodium diethylamide, and sodium dicyclohexylamide;
    the suitable aprotic solvent is either an ether solvent or a combination of an ether solvent with one or more hydrocarbon solvents wherein the ether solvent is selected from the group consisting of:
        tetrahydrofuran, diethylether, t-butylmethylether, and 1,2-dimethoxyethane; and
    the hydrocarbon solvent is selected from the group consisting of:
        butane, pentane, hexane, heptane, benzene, toluene, and xylene;
    the suitable concentration solvent is toluene or methylcyclohexane; and
    the suitable quenching agent is selected from the group consisting of:
    ammonium chloride, ammonium acetate, ammonium sulfate, acetic acid, propionic acid, hydrochloric acid, sulfuric acid and water.

7. A process according to claim 6 for the synthesis of cyclopropylacetylene, wherein the 5-halo-1-pentyne is 5-chloro-1-pentyne.

8. A process according to claim 6 for the synthesis of cyclopropylacetylene, wherein the suitable strong base is n-hexyllithium.

9. A process according to claim 6 for the synthesis of cyclopropylacetylene, wherein the suitable quenching agent is ammonium chloride.

10. A process according to claim 6 for the synthesis of cyclopropylacetylene, wherein the suitable aprotic solvent is either tetrahydrofuran or a combination of tetrahydrofuran and hexane.

11. A process according to claim 6 for the synthesis of cyclopropylacetylene, wherein:
    the 5-halo-1-pentyne is 5-chloro-1-pentyne;
    the suitable strong base is n-hexyllithium;
    the suitable concentration solvent is toluene; and
    the suitable quenching agent is ammonium chloride.

12. A process according to claim 5 for synthesis of cyclopropylacetylene, comprising:
    (1) contacting one equivalent of 5-halo-1-pentyne with about two to about three equivalents of a suitable strong base in a suitable aprotic solvent at a temperature of between about −10° C. and about 30° C. for sufficient time to form a reaction mixture and effect greater than about 95% formation of cyclopropylacetylide;

(2) adding a concentration solvent;

(3) distilling the reaction mixture under vacuum at a temperature of between about 20° C. and about 65° C. to reduce the volume to about one third the volume before distillation under vacuum;

(4) contacting the reaction mixture with a suitable quenching agent to effect formation of cyclopropylacetylene;

(5) drying the reaction mixture to a water content of between about 0 to about 500 parts per million; and (6) purifying the desired product by distillation.

13. A process according to claim 12 for the synthesis of cyclopropylacetylene, wherein:

the suitable strong base is selected from the group consisting of:
n-hexyllithium, n-butyllithium, s-butyllithium, t-butyllithium, phenyllithium, sodium amide, potassium amide, lithium amide, sodium diethylamide, and sodium dicyclohexylamide;

the suitable aprotic solvent is either an ether solvent or a combination of an ether solvent with one or more hydrocarbon solvents wherein the ether solvent is selected from the group consisting of:
tetrahydrofuran, diethylether, t-butylmethylether, and 1,2-dimethoxyethane; and the hydrocarbon solvent is selected from the group:
butane, pentane, hexane, heptane, benzene, toluene, and xylene;

the suitable concentration solvent is toluene or methylcyclohexane; and the suitable quenching agent is selected from the group consisting of:
ammonium chloride, ammonium acetate, ammonium sulfate, acetic acid, propionic acid, hydrochloric acid, sulfuric acid and water.

14. A process according to claim 13 for the synthesis of cyclopropylacetylene, wherein the 5-halo-1-pentyne is 5-chloro-1-pentyne.

15. A process according to claim 13 for the synthesis of cyclopropylacetylene, wherein the suitable strong base is n-hexyllithium.

16. A process according to claim 13 for the synthesis of cyclopropylacetylene, wherein the suitable quenching agent is ammonium chloride.

17. A process according to claim 13 for the synthesis of cyclopropylacetylene, wherein the suitable aprotic solvent is either tetrahydrofuran or a combination of tetrahydrofuran and hexane.

18. A process according to claim 13 for the synthesis of cyclopropylacetylene, wherein:

the 5-halo-1-pentyne is 5-chloro-1-pentyne;

the suitable strong base is n-hexyllithium;

the suitable concentration solvent is toluene; and the suitable quenching agent is ammonium chloride.

19. A process for synthesis of cyclopropylacetylene, said process comprising:

(1) contacting one equivalent of 5-chloro-1-pentyne with about two to about three equivalents of a n-hexyllithium in either tetrahydrofuran or a combination of tetrahydrofuran/hexane at a temperature of between about −10° C. and about 30° C. for sufficient time to form a reaction mixture and effect greater than about 95% formation of cyclopropylacetylide;

(2) adding toluene;

(3) distilling the reaction mixture under vacuum at a temperature of between about 20° C. and about 65° C. to reduce the volume to about one third the volume before distillation under vacuum;

(4) contacting the reaction mixture with a ammonium chloride to effect formation of cyclopropylacetylene;

(5) drying the reaction mixture to a water content of between about 1 to about 400 parts per million; and (6) purifying the desired product by distillation.

* * * * *